(12) United States Patent
Allen et al.

(10) Patent No.: US 10,493,074 B2
(45) Date of Patent: Dec. 3, 2019

(54) SPECIFIC TRIFLUOROETHYL QUINOLINE ANALOGUE FOR USE IN THE TREATMENT OF SJÖGREN'S SYNDROME

(71) Applicant: UCB Biopharma SPRL, Brussels (BE)

(72) Inventors: Rodger Anthony Allen, Slough (GB); Francesca Barone, Birmingham (GB); William Anthony Fahy, Slough (GB); Saba Nayar, Birmingham (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/565,866

(22) PCT Filed: Apr. 20, 2016

(86) PCT No.: PCT/EP2016/058810
§ 371 (c)(1),
(2) Date: Oct. 11, 2017

(87) PCT Pub. No.: WO2016/170014
PCT Pub. Date: Oct. 27, 2016

(65) Prior Publication Data
US 2018/0092921 A1 Apr. 5, 2018

(30) Foreign Application Priority Data

Apr. 21, 2015 (GB) .................................. 1506786.1

(51) Int. Cl.
*A61K 31/519* (2006.01)
*A61K 9/00* (2006.01)
*A61K 31/4709* (2006.01)

(52) U.S. Cl.
CPC ............ *A61K 31/519* (2013.01); *A61K 9/006* (2013.01); *A61K 9/0014* (2013.01); *A61K 9/0031* (2013.01); *A61K 9/0048* (2013.01); *A61K 9/0073* (2013.01); *A61K 31/4709* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 2012/0065183 A1* | 3/2012 | Cooke | ................... | C07D 471/04 514/210.18 |
| 2014/0371246 A1* | 12/2014 | Evarts | ................... | A61K 31/517 514/266.21 |

FOREIGN PATENT DOCUMENTS

| WO | 2012/032334 A1 | 3/2012 | | |
|---|---|---|---|---|
| WO | WO 2012/032334 | * | 3/2012 | ........... C07D 471/04 |

OTHER PUBLICATIONS

Nayar et al., "Phosphatidylinositol-3-kinase Delta Parthway a Novel Therapeutic Target for Sjögren's Syndrome", Arthritis and Rheumatology, 2015, 67(10), Abstract No. 1053, 2 pages.
Anonymous, "UCB Proof of Concept Study in Patients with Primary Sjögren's Syndrome", 2015, XP002758921, retrieved from the Internet: URL:https://clinicaltrials.gov/ct2/show/record/NCT02610543?term=ucb_5857&rank=3, 11 pages.
Bowman et al., "Biologic Treatments in Sjögren's Syndrome", Presse Medicale, 2012, 41(9), e495-e509.
Baudouin et al., "Current Treatments of Xerophthalmia in Sjögren's Syndrome // Traitements actuels de la xerophthalmia in Sjögren's syndrome", La Revue de Medecine Interne, 2004, 25(5), 376-382.
Yager et al., "Inhibition of phosphatidylinositol-3-kinase delta reduces psoriatic T cell activity", Journal of Investigative Dermatology, 2014, 134(2), 418, p. s73.

* cited by examiner

*Primary Examiner* — Craig D Ricci
(74) *Attorney, Agent, or Firm* — McDonnell Boehnen Hulbert & Berghoff LLP

(57) ABSTRACT

N-{(R)-1-[8-Chloro-2-(1-oxypyridin-3-yl)-quinolin-3-yl]-2,2,2-trifluoroethyl}-pyrido[3,2-d]pyrimidin-4-ylamine is effective in the treatment and/or prevention of Sjögren's syndrome.

8 Claims, 6 Drawing Sheets

Figure 1:
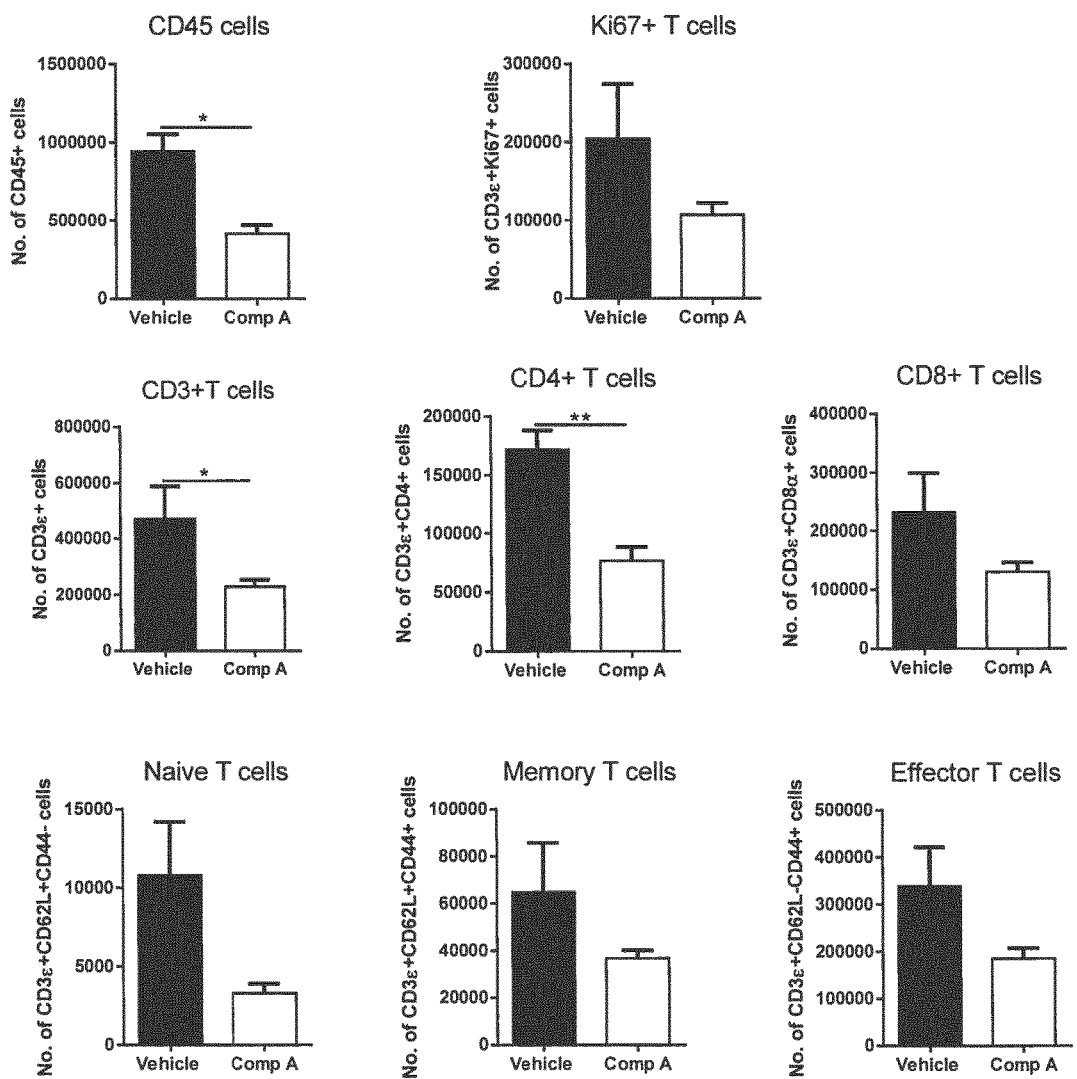
Figure 1:
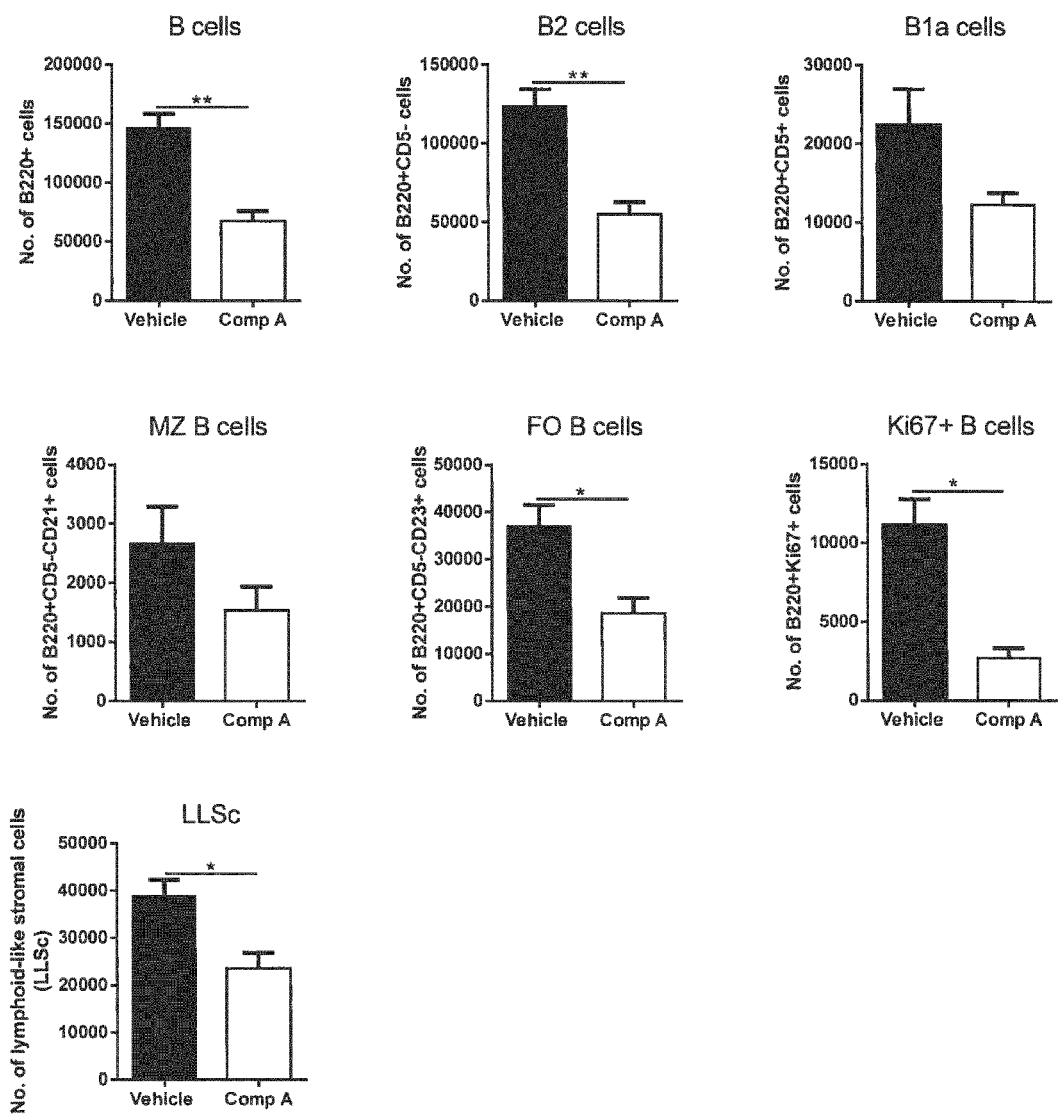

SPECIFIC TRIFLUOROETHYL QUINOLINE ANALOGUE FOR USE IN THE TREATMENT OF SJÖGREN'S SYNDROME

This application is a U.S. national phase application under 35 USC 371 of International Patent Application no. PCT/EP2016/058810, filed Apr. 20, 2016, which claims the benefit of Great Britain Application no. 1506786.1, filed Apr. 21, 2015.

The present invention relates to the new therapeutic use of a known chemical compound. More particularly, the present invention concerns the use of a specific substituted quinoline derivative comprising a fluorinated ethyl side-chain in the treatment of Sjögren's syndrome.

N-{(R)-1-[8-Chloro-2-(1-oxypyridin-3-yl)quinolin-3-yl]-2,2,2-trifluoroethyl}-pyrido[3,2-d]pyrimidin-4-ylamine is specifically disclosed in WO 2012/032334. The compounds described in that publication are stated to be of benefit as pharmaceutical agents, especially in the treatment of adverse inflammatory, autoimmune, cardiovascular, neurodegenerative, metabolic, oncological, nociceptive and ophthalmic conditions.

There is no specific disclosure or suggestion in WO 2012/032334, however, that the compounds described therein might be beneficial in the treatment of Sjögren's syndrome.

Sjögren's syndrome is a chronic autoimmune disorder in which immune cells attack and destroy the exocrine glands, chiefly the salivary and lachrymal glands. The characteristic symptom of Sjögren's syndrome is a generalised dryness, particularly of the mouth (xerostomia) and eyes (xerophthalmia; keratoconjunctivitis sicca). Sjögren's syndrome may cause skin, nose and vaginal dryness, and may affect other bodily organs including the kidneys, blood vessels, lungs, liver, pancreas, brain and peripheral nervous system. Sjögren's syndrome is clinically classified either as a 'primary' disorder (occurring by itself), or as a 'secondary' condition, whereby it occurs in association with at least one other connective tissue disease such as systemic lupus erythematosus or rheumatoid arthritis.

It is believed that Sjögren's syndrome occurs in up to 3% of the population, with little or no variation in geographical prevalence. Females are nine times more likely than males to develop the disease. The average age of onset is 40-60, with the prevalence of Sjögren's syndrome generally increasing with age.

Sjögren's syndrome can damage vital organs of the body with symptoms that may stabilise, worsen or go into remission. Some patients may experience only mild symptoms of dry eyes and mouth, whilst others suffer debilitating cycles of good health followed by severe disease. Whilst many patients can treat their symptoms individually, others are obliged to endure blurred vision, constant eye discomfort, recurrent mouth infections, swollen parotid glands, hoarseness, and difficulty in swallowing and eating. Debilitating fatigue and joint pain can seriously reduce quality of life.

There is currently no known cure for Sjögren's syndrome, nor is there an effective treatment to restore gland secretion. Existing treatment is generally symptomatic and supportive, and includes moisture replacement therapy (e.g. to relieve the symptoms of eye and mouth dryness) and various forms of lubrication. Prescription medicines are available, including cyclosporine to aid in treating chronic dry eye, and cevimeline or pilocarpine to aid in stimulating salivary flow. Anti-inflammatory agents, such as methotrexate and hydroxychloroquine, have also been prescribed for the amelioration of musculoskeletal symptoms. None of the currently available medications is ideal, however, if only because of their wide range of serious side-effects.

It has now been found, surprisingly, that N-{(R)-1-[8-chloro-2-(1-oxypyridin-3-yl)-quinolin-3-yl]-2,2,2-trifluoroethyl}pyrido[3,2-d]pyrimidin-4-ylamine is effective in an in vivo animal model of Sjögren's syndrome.

The present invention accordingly provides N-{(R)-1-[8-chloro-2-(1-oxypyridin-3-yl)quinolin-3-yl]-2,2,2-trifluoroethyl}pyrido[3,2-d]pyrimidin-4-ylamine of formula (A):

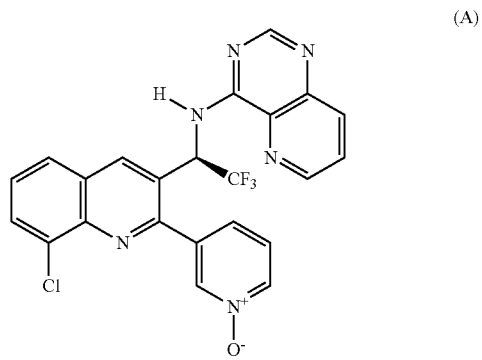 [SMILES: [O-][n+]1cccc(-c2nc3c(Cl)cccc3cc2[C@@H](Nc2ncnc3cccnc23)C(F)(F)F)c1]

(A)

or a pharmaceutically acceptable salt thereof, for use in the treatment and/or prevention of Sjögren's syndrome.

The present invention also provides a method for the treatment and/or prevention of Sjögren's syndrome, which method comprises administering to a patient in need of such treatment an effective amount of N-{(R)-1-[8-chloro-2-(1-oxypyridin-3-yl)quinolin-3-yl]-2,2,2-trifluoroethyl}pyrido[3,2-d]pyrimidin-4-ylamine of formula (A) as depicted above, or a pharmaceutically acceptable salt thereof.

The present invention also provides the use of N-{(R)-1-[8-chloro-2-(1-oxypyridin-3-yl)quinolin-3-yl]-2,2,2-trifluoroethyl}pyrido[3,2-d]pyrimidin-4-ylamine of formula (A) as depicted above, or a pharmaceutically acceptable salt thereof, for the manufacture of a medicament for the treatment and/or prevention of Sjögren's syndrome.

For the effective treatment and/or prevention of Sjögren's syndrome, a pharmaceutical composition may be provided which comprises N-{(R)-1-[8-chloro-2-(1-oxypyridin-3-yl)quinolin-3-yl]-2,2,2-trifluoroethyl}pyrido[3,2-d]pyrimidin-4-ylamine of formula (A) as depicted above, or a pharmaceutically acceptable salt thereof, in association with a pharmaceutical carrier. Typical pharmaceutical compositions may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges, capsules, solutions, syrups or suspensions, or they may be presented as a dry product for constitution with water or other suitable vehicle before use. For buccal administration, the compositions may take the form of tablets or lozenges. For parenteral administration, the compositions may be formulated for injection, e.g. by bolus injection or infusion, for subcutaneous administration, or as a long-acting formulation, e.g. a depot preparation which may be administered by implantation or by intramuscular injection; formulations for injection may be presented in unit dosage form, e.g. in glass ampoules or multi-dose containers, e.g. glass vials, and may take such forms as suspensions, solutions or emulsions in oily or aqueous vehicles, or the active ingredient may be in powder form for constitution with a suitable vehicle, e.g. sterile pyrogen-free water, before use. For nasal administration or administration by inhalation, the composition may take the form of an aerosol spray presentation for pressurised packs or a nebuliser. For topical administration, the composition may take the form of an ointment or lotion. For ophthalmic administration the composition may be formulated as a micronized suspension or an ointment. For rectal administration, the compositions may be formulated as suppositories.

The compositions may be formulated by conventional methods well known in the pharmaceutical art, for example as described in *Remington: the Science and Practice of Pharmacy*, Pharmaceutical Press, 21$^{st}$ Edition, 2011.

For use in the treatment and/or prevention of Sjögren's syndrome, N-{(R)-1-[8-chloro-2-(1-oxypyridin-3-yl)quinolin-3-yl]-2,2,2-trifluoroethyl}pyrido[3,2-d]pyrimidin-4-ylamine, or a pharmaceutically acceptable salt thereof, may suitably be administered at a daily dosage of about 1 ng/kg to 1000 mg/kg, generally about 2 ng/kg to 500 mg/kg, typically about 5 ng/kg to 200 mg/kg, appositely about 10 ng/kg to 100 mg/kg, ideally about 10 ng/kg to 50 mg/kg, more particularly about 10 ng/kg to 40 mg/kg, of body weight. The active ingredient will typically be administered on a regimen of 1 to 4 times a day.

If desired, N-{(R)-1-[8-chloro-2-(1-oxypyridin-3-yl)quinolin-3-yl]-2,2,2-trifluoro-ethyl}pyrido[3,2-d]pyrimidin-4-ylamine, or a pharmaceutically acceptable salt thereof, may be co-administered with another pharmaceutically active agent, e.g. an anti-inflammatory molecule such as methotrexate or hydroxychloroquine.

Specific aspects of the invention will now be described. N-{(R)-1-[8-Chloro-2-(1-oxypyridin-3-yl)quinolin-3-yl]-2,2,2-trifluoroethyl}-pyrido[3,2-d]pyrimidin-4-ylamine [hereinafter referred to as "Compound (A)"] was investigated in vivo in an inducible model of ectopic lymphoneogenesis in murine salivary glands that mimics Sjögren's syndrome. The results obtained are depicted in the accompanying drawings, in which:

FIG. 1 shows a FACS (fluorescence-activated cell sorting) analysis of lymphocyte profile at day 15 post-cannulation in salivary glands of mice treated with vehicle or Compound (A) prophylactically from day 0.

| |
|---|
| Vehicle: n = 3 mice |
| Compound (A): n = 5 mice |
| MZ B cells = Marginal Zone B cells |
| FO B cells = Follicular B cells |

* $p < 0.05$
** $p < 0.01$

Figure 2:
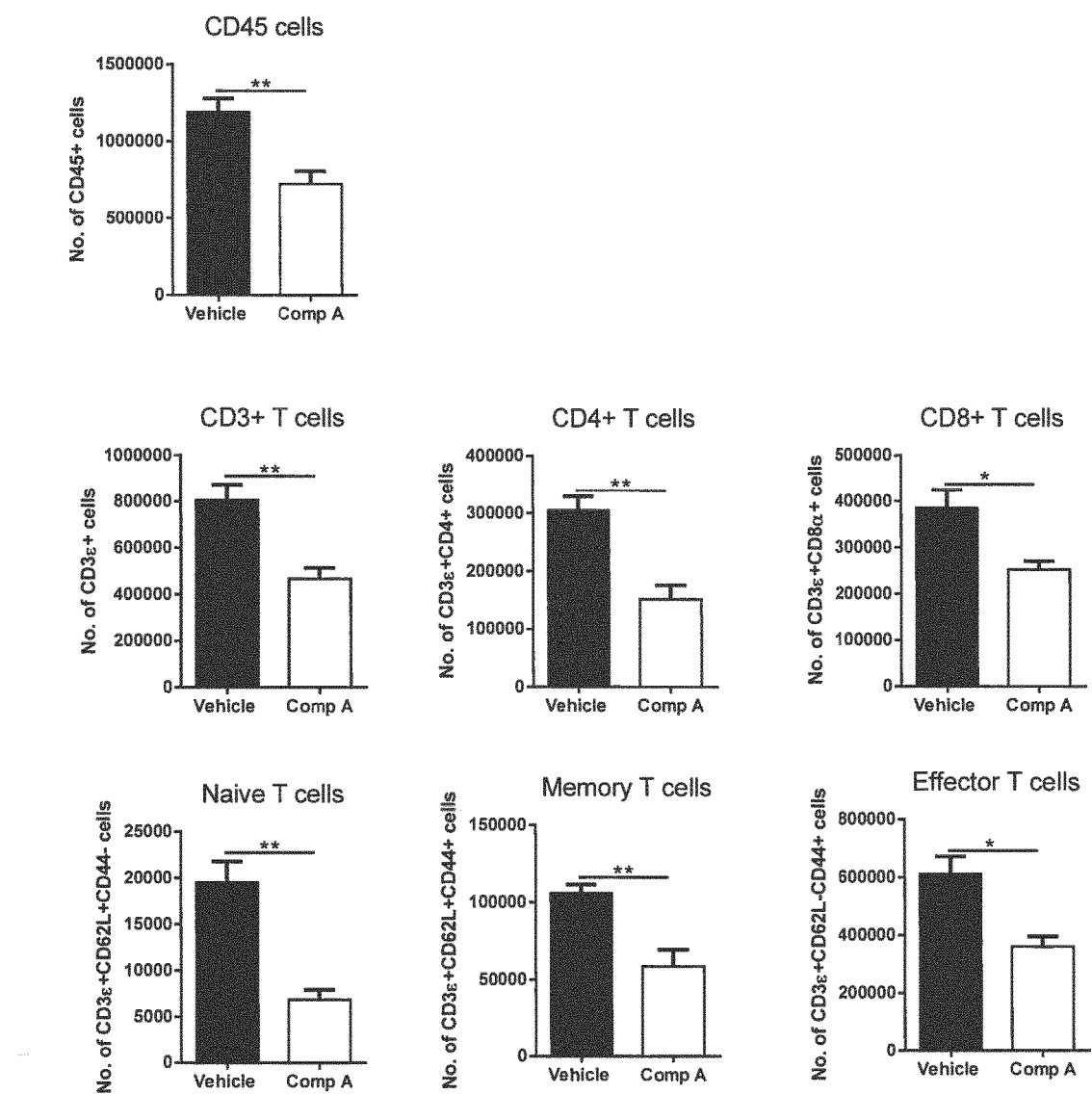
Figure 2:
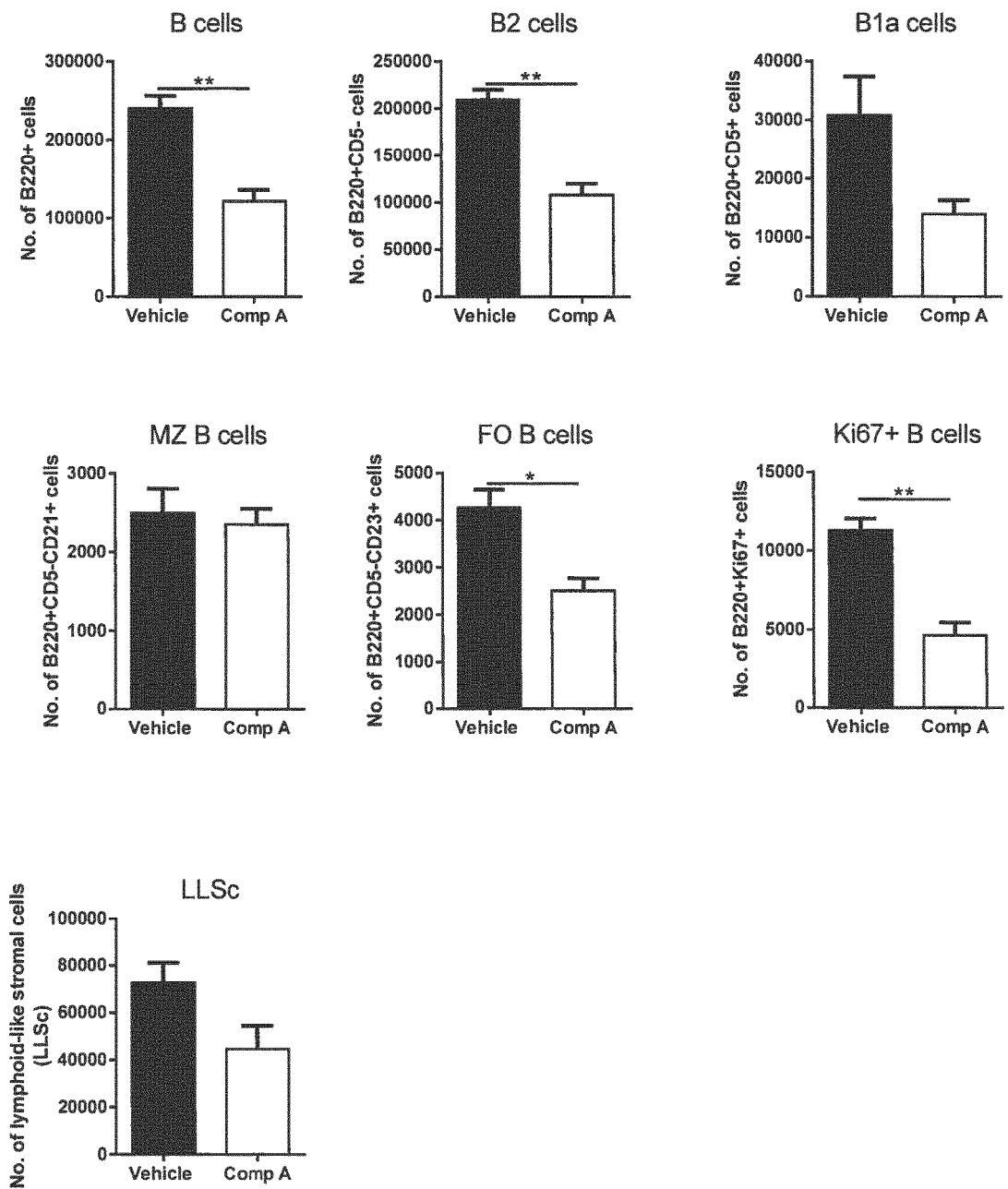

FIG. 2 shows a FACS analysis of lymphocyte profile at day 15 post-cannulation in salivary glands of mice treated with vehicle or Compound (A) therapeutically from day 3 post-cannulation.

| |
|---|
| Vehicle: n = 4 mice |
| Compound (A): n = 5 mice |
| MZ B cells = Marginal Zone B cells |
| FO B cells = Follicular B cells |

* $p < 0.05$
** $p < 0.01$

Figure 3:
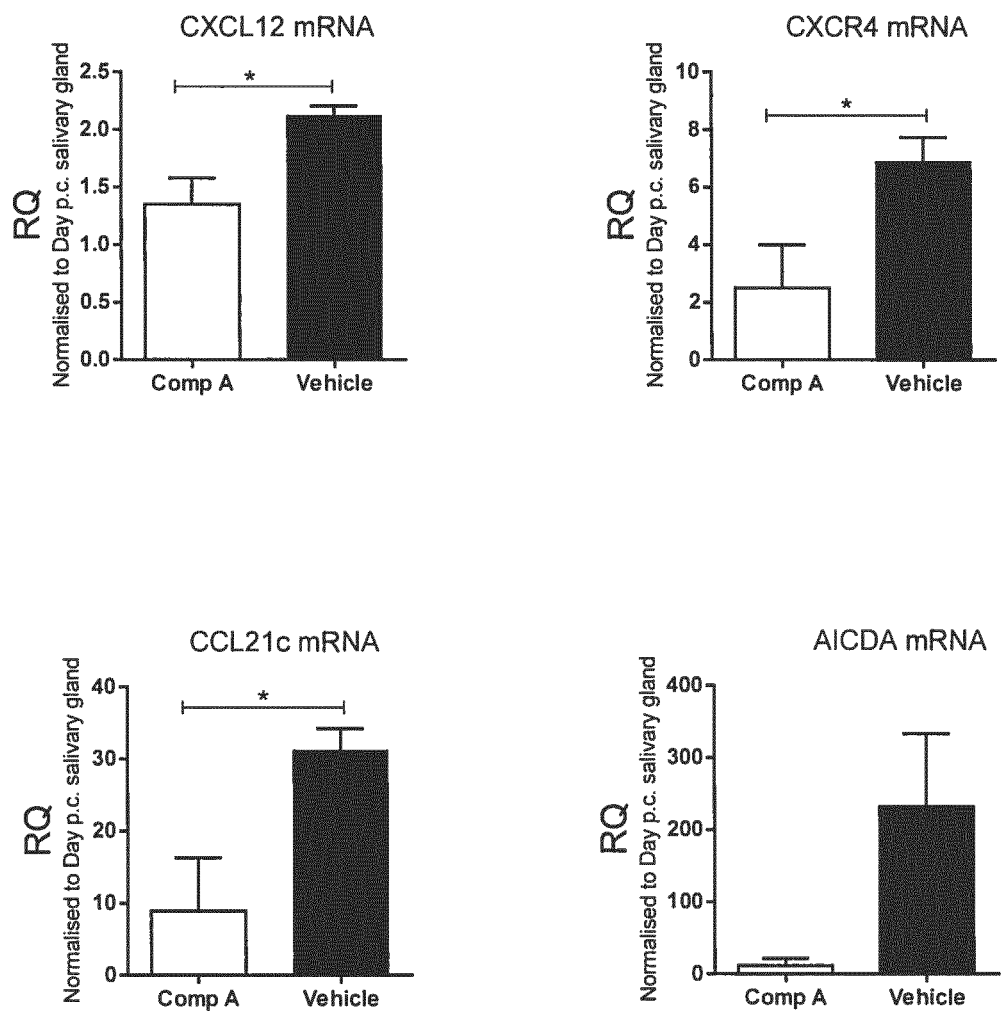

FIG. 3 shows the gene expression of TLO (tertiary lymphoid organ) associated genes at day 15 post-cannulation in salivary glands of mice treated with vehicle or Compound (A) prophylactically from day 0. Quantitative RT-PCR analysis of mRNA transcripts coding for indicated genes, normalised to housekeeping gene. The relative expression values presented as RQ were calibrated with day 0 post-cannulation salivary gland values.

| |
|---|
| Vehicle: n = 3 mice |
| Compound (A): n = 2 mice |

* $p < 0.05$

Figure 4:
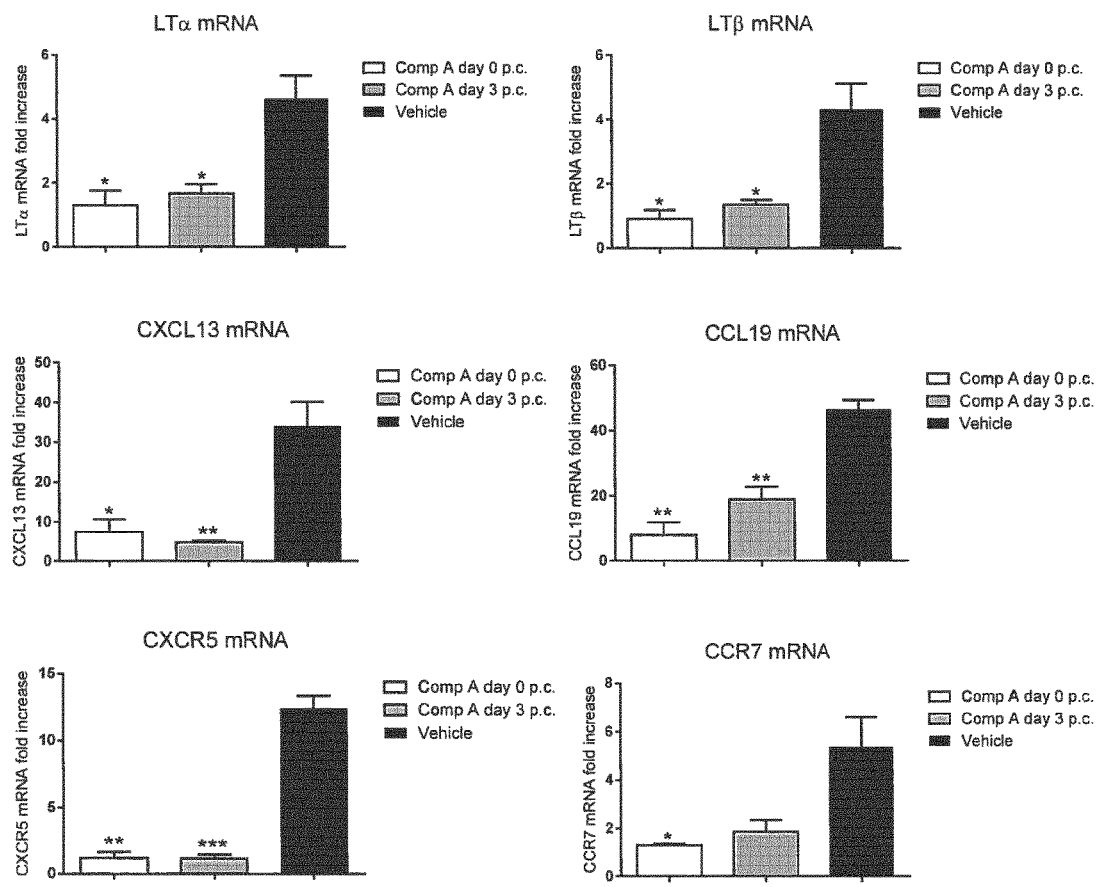

FIG. 4 shows the gene expression of TLO associated genes at day 15 post-cannulation in salivary glands of mice treated with vehicle or Compound (A) prophylactically from day 0 or therapeutically from day 3 post-cannulation.

| |
|---|
| Vehicle: n = 3 mice |
| Compound (A), day 0 post-cannulation: n = 3 mice |
| Compound (A), day 3 post-cannulation: n = 3 mice |

* $p < 0.05$
** $p < 0.01$
*** $p < 0.001$

Method

Compound (A) was assessed in the in vivo murine model of inducible ectopic lymphoid tissue formation described by M. Bombardieri et al. in *J. Immunol.*, 2012, 189, 3767-3776, which is a recognised animal model of Sjögren's syndrome.

Briefly, wild type (C57BL/6) mice were given replication-defective adenovirus 5 (AdV5) ($10^8$ p.f.u.) via retrograde cannulation of submandibular gland excretory ducts and sacrificed at specific time points post-cannulation. Compound (A), or vehicle control, was administered by gavage daily both prophylactically and therapeutically, starting at either day 0 or day 3 post-cannulation respectively. In order to assess immune cell status in isolated murine salivary glands, flow cytometry on single cell suspensions and quantitative real time PCR were used to evaluate protein and mRNA expression in the samples.

Enzymatic Digestion of Salivary Glands and Flow Cytometry

Stromal Cell Digestion

Replication-defective AdV5-infused salivary glands from mice dosed with either Compound (A) or vehicle were isolated from culled mice at different time points. Glands were dissected and placed in RPMI-1640 (with 2% FCS) (1 mL) on ice. Once all salivary glands were collected, RPMI-1640 was removed and replaced with enzyme mix (RMPI with 2% FCS, 0.8 mg/mL Dispase, 0.2 mg/mL Collagenase P, and 0.1 mg/mL DNase I) (2 mL). Salivary glands were cut into small pieces and tubes were incubated at 37° C. in a water bath, with magnetic stirrers. After 20 minutes, salivary gland fragments were very gently pipetted, using a 1 mL pipette, to disrupt the tissue further and release most cells. The mixture was replaced in the water bath and large fragments were allowed to settle for 30 s, after which time the enzyme mix was removed. Ice-cold FACS buffer (0.5% BSA, 2 mM EDTA in PBS) (10 mL) was added and centrifuged (1800 rpm, 4 minutes, 4° C.). After centrifugation, fresh enzyme mix (2 mL) was added to the digestion tube. The contents were gently mixed using a 1 mL pipette, and incubated, with regular gentle mixing using a 1 mL pipette. After 10 minutes, the cells were mixed vigorously for 30 s using a 1 mL pipette. Fragments were again allowed to settle, the supernatant was removed and added to the previously spun cell pellet, and fresh enzyme mix (2 mL) was added to the digestion tube. The digestion mix was then vigorously mixed using a 1 mL pipette every 5 minutes until, when held up to light, it was clear that all remaining salivary gland fragments were completely digested. Supernatants were centrifuged after each removal (1800 rpm, 4 minutes, 4° C.) until, finally, each collection tube contained the entire cellular contents of the salivary gland. Cells were filtered through 70 µm nylon mesh and counted using a haemocytometer.

Flow Cytometry Analysis

Single cell suspensions were incubated with diluted antibodies (100 µL) for 30 minutes at 4° C. in ice-cold FACS buffer (0.5% BSA, 2 mM EDTA in PBS) with 'cocktails' of the following antibodies: CD45 PERCPCY5.5 (1:300) or CD45 eFluor780 (1:800) clone 30-F11, CD3e PECY7 or FITC (1:100) clone 145-2C11, CD4 efluor450 (1:100) clone RM4-5, CD62L PE (1:500) clone MEL-14, CD44 FITC (1:500) clone IM7, CD8a APC (1:400) clone 53-6.7, B220 FITC (1:200) or B220 efluor450 (1:50) clone RA3-6B2, CD23 PE (1:200) clone B3B4, CD19 PE (1:200) or APC-CY7 (1:100) clone 1D3 and CD5 FITC (1:100) clone 53-7.3 (all from eBiosciences) and CD21 APC (1:50) clone 7G6 (from BD Biosciences). Intracellular staining for Ki67 was performed by using the Fixation/Permeabilization Buffer Set (eBioscience) according to the manufacturer's protocol. In brief, following surface staining with cocktails of desired antibodies, cells were washed in FACS buffer, re-suspended in Fixation/Permeabilization Buffer (eBioscience) (350 µL) and incubated for 30 minutes at 4° C. Cells were washed twice with Permeabilization Buffer (eBiosciences) at 1800 rpm for 4 minutes and subsequently incubated with Ki67 Alexa-Fluor647 (1:50) clone B56 (BD Biosciences) at 4° C. for 20 minutes. Cells were then washed with wash buffer, resuspended in FACS buffer, and analyzed using a Cyan-ADP (Dako) with forward/side scatter gates set to exclude non-viable cells. Data were analyzed with FlowJo software (Tree Star).

Results

A significant decrease in the number of T and B cells was observed in vivo in cannulated salivary glands of mice treated prophylactically with Compound (A), by comparison with vehicle treated mice, as confirmed by flow cytometry on isolated lymphocytes (FIG. 1). Similarly, a significant decrease in the number of T and B cells was observed in vivo in cannulated salivary glands of mice treated therapeutically with Compound (A) from day 3 post-cannulation, by comparison with vehicle treated mice, as confirmed by flow cytometry on isolated lymphocytes (FIG. 2).

Gene expression profile of TLO associated genes was also significantly inhibited in mice treated prophylactically with Compound (A) (FIGS. 3 & 4). This decrease was conserved in mice treated therapeutically from day 3 post-cannulation (FIG. 4).

CONCLUSION

These studies demonstrate that Compound (A) is effective, when dosed either prophylactically or therapeutically, in disaggregation of the inflammatory foci and resolution of salivary gland inflammation in a recognised in vivo animal model of Sjögren's syndrome.

The invention claimed is:

1. A method for the treatment of Sjögren's syndrome, which method comprises administering to a patient in need of such treatment an effective amount of N-{(R)-1-[8-chloro-2-(1-oxypyridin-3-yl)quinolin-3-yl]-2,2,2-trifluoroethyl}pyrido[3,2-d]-pyrimidin-4-ylamine, or a pharmaceutically acceptable salt thereof.

2. The method according to claim 1, wherein the Sjögren's syndrome is primary Sjögren's syndrome.

3. The method according to claim 1, wherein the N-{(R)-1-[8-chloro-2-(1-oxypyridin-3-yl)quinolin-3-yl]-2,2,2-trifluoroethyl}pyrido[3,2-d]-pyrimidin-4-ylamine, or a pharmaceutically acceptable salt thereof is administered in the form of a pharmaceutical composition comprising the N-{(R)-1-[8-chloro-2-(1-oxypyridin-3-yl)quinolin-3-yl]-2,2,2-trifluoroethyl}pyrido[3,2-d]-pyrimidin-4-ylamine, or a pharmaceutically acceptable salt thereof, and a pharmaceutical carrier.

4. The method according to claim 3, wherein the N-{(R)-1-[8-chloro-2-(1-oxypyridin-3-yl)quinolin-3-yl]-2,2,2-trifluoroethyl}pyrido[3,2-d]-pyrimidin-4-ylamine, or a pharmaceutically acceptable salt thereof is administered in the form of a pharmaceutical composition comprising the N-{(R)-1-[8-chloro-2-(1-oxypyridin-3-yl)quinolin-3-yl]-2,2,2-trifluoroethyl}pyrido[3,2-d]-pyrimidin-4-ylamine, or a pharmaceutically acceptable salt thereof, and a pharmaceutical carrier.

5. The method according to claim 4, wherein the pharmaceutical composition is adapted for oral administration.

6. The method according to claim 5, wherein the pharmaceutical composition is adapted for oral administration.

7. The method according to claim 4, wherein the pharmaceutical composition is adapted for buccal, parenteral, nasal, topical, ophthalmic or rectal administration, or for inhalation or insufflation.

8. The method according to claim 5, wherein the pharmaceutical composition is adapted for buccal, parenteral, nasal, topical, ophthalmic or rectal administration, or for inhalation or insufflation.

* * * * *